(12) United States Patent
Karslo

(10) Patent No.: US 7,667,469 B2
(45) Date of Patent: Feb. 23, 2010

(54) METHOD AND APPARATUS FOR DRY TESTING NON-CONDUCTIVE CONTAINERS FOR CARRYING PEOPLE

(75) Inventor: William R. Karslo, Glennville, GA (US)

(73) Assignee: HKH Dielectric, LLC, Horsham, PA (US)

( * ) Notice: Subject to any disclaimer, the term of this patent is extended or adjusted under 35 U.S.C. 154(b) by 208 days.

(21) Appl. No.: 11/829,670

(22) Filed: Jul. 27, 2007

(65) Prior Publication Data

US 2008/0024144 A1 Jan. 31, 2008

Related U.S. Application Data

(60) Provisional application No. 60/820,545, filed on Jul. 27, 2006.

(51) Int. Cl.
*G01R 27/08* (2006.01)

(52) U.S. Cl. ....................................... 324/691

(58) Field of Classification Search ................... 324/691
See application file for complete search history.

(56) References Cited

U.S. PATENT DOCUMENTS

| | | | | |
|---|---|---|---|---|
| 5,519,565 A * | 5/1996 | Kalt et al. | .................... | 361/280 |
| 5,945,832 A * | 8/1999 | Harvey et al. | ................ | 324/693 |
| 5,974,750 A * | 11/1999 | Landin et al. | ............ | 52/396.01 |
| 6,691,563 B1 * | 2/2004 | Trabelsi et al. | .................. | 73/73 |
| 6,784,405 B2 * | 8/2004 | Flugstad et al. | ............. | 219/497 |
| 2004/0177685 A1 * | 9/2004 | Yokura et al. | ............ | 73/335.04 |

* cited by examiner

*Primary Examiner*—Jeff Natalini
(74) *Attorney, Agent, or Firm*—Volpe and Koenig, PC

(57) ABSTRACT

A method and apparatus for dry testing non-conductive containers for carrying people are disclosed. Two conductive materials placed on opposite sides of a material being tested. High voltage is applied to one of the conductive materials while a ground lead is attached to the other conductive material. Electric current is measured from the grounded conductive material to identify any breakdown of the dielectric properties of the material being tested.

6 Claims, 5 Drawing Sheets

METHOD AND APPARATUS FOR DRY TESTING NON-CONDUCTIVE CONTAINERS FOR CARRYING PEOPLE

CROSS REFERENCE TO RELATED APPLICATIONS

This application claims the benefit of U.S. provisional application 60/820,545 filed Jul. 27, 2006, which is incorporated by reference as if fully set forth.

FIELD OF INVENTION

The present invention generally relates to dielectric testing of bucket liners for lift equipment.

BACKGROUND

To maintain utility lines, utility companies and contractors use trucks with lift equipment to reach overhead lines carrying various utilities. Frequently service vehicles are equipped with lift equipment that can hold and carry a person from street level to the utility line. This is accomplished by attaching a boom to the chassis of the vehicle. At the end of the boom, a bucket is attached into which a person can stand and be lifted by the boom to an overhead location. Non conductive liners are designed that can be inserted into the bucket and insulate the occupant from high voltage that is frequently near overhead utility lines. It can be appreciated that the use of such equipment can expose the worker on the lift equipment to high voltage sources that may be conducted through the chassis of the vehicle and its lift equipment possibly shocking or electrocuting the worker should the equipment come into contact with the voltage source. To preserve safety of line workers, safety guidelines and precautions have been established to insulate the worker from exposure to high voltage sources while using lift equipment. Standards have been established for vehicle mounted elevating and rotating devices. These are covered in the American National Standards Institute (ANSI) published standard A92.2-2001. In particular, sections 5.4.2.5 and 5.4.3.5 relate to the testing of insulating liners that are inserted into buckets designed for carrying workers in an aerial device. ANSI A92.2-2001 Section 5.4.2.5 pertains to the testing of liners for design, qualification and quality assurance during manufacture, while ANSI A92.2-2001 Section 5.4.3.5 pertains to the periodic testing of liners is use in the field.

Current standards dictate that testing of insulating liners be carried out in a conductive liquid. Typically water is used for this type of testing. Water tanks used to perform this type of testing are bulky and require large volumes of water. Testing the dielectric properties of a liner requires that both the inner and outer surfaces be submerged to within six inches of the top of the liner. It can be appreciated that the structure to support such a volume of water must be large and heavy. This creates issues of storage and portability and makes testing in the field cumbersome. The electrification of water also creates an electrical hazard should anything happen during the testing process that would allow the leakage or spillage of water while exposed to a high voltage. Because of its property as a fluid the voltage in the electrified water can be distributed to unintended areas if a spill or leak occurs. The danger of exposure to electricity is heightened if the earth where the test is performed is damp and capable of conducting the voltage from the testing process. Electric current can flow through the damp ground to persons performing the testing procedure. Wet testing also necessitates the disposal of large volumes of water containing residue from the liner that may be exposed to the elements and the grease and dirt associated with the climbing in and out of a line worker. The water may also contain foreign matter as a result of the performance of the testing procedure. This water is generally disposed of by draining into the ground or dumped into a storm drain. Many gallons of clean water are wasted and the environment exposed to possible contamination. It would be beneficial therefore, to have the ability to test the dielectric properties of insulating liners without the use of liquid.

SUMMARY

The present invention is a method and apparatus for dry testing non-conductive containers for carrying people. Two conductive materials placed on opposite sides of a material being tested. High voltage is applied to one of the conductive materials while a ground lead is attached to the other conductive material. Electric current is measured from the grounded conductive material to identify any breakdown of the dielectric properties of the material being tested.

BRIEF DESCRIPTION OF THE DRAWING(S)

A more detailed understanding of the invention may be had from the following description of a preferred embodiment, given by way of example and to be understood in conjunction with the accompanying drawing(s) wherein.

DETAILED DESCRIPTION OF THE PREFERRED EMBODIMENT(S)

Throughout this description, the term sock is used to describe a conductive material disposed along a surface of a container. The material is formed to closely follow the contours of the container and is preferably fitted to an outer surface and inner surface of the container. The container, in one embodiment of the present invention, is an insulating liner of a bucket as described above. For example, the conductive material may be a woven polyester fabric having a conductive plating material. While an example is provided, it is important to note that the conductive material may be any type of conductive material. The conductive material is preferably any type of conductive material capable of enabling dielectric testing of an insulating liner without the use of water.

Figure 1:
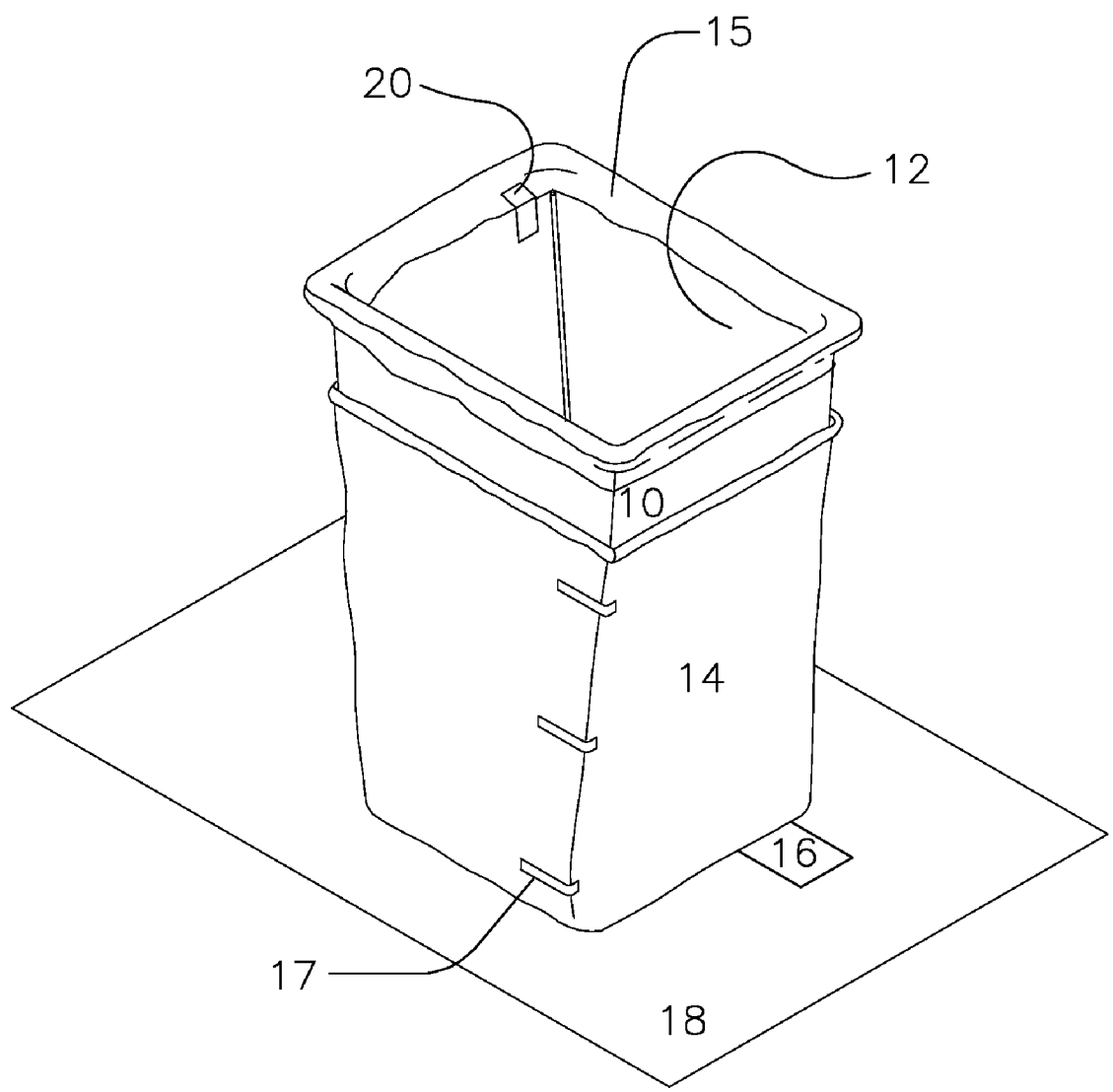
FIG. 1 is a perspective view of an insulating liner sitting on an arc suppression blanket wherein the insulating liner has conductive socks disposed along its inner and outer surfaces in accordance with an embodiment of the invention.

Referring now to FIG. 1, there is shown insulating liner 10 sitting on an arc suppression blanket 18 wherein the insulating liner 10 has conductive socks 12, 14 disposed along inner and outer surfaces, respectively, of the insulating liner 10 in accordance with an embodiment of the invention. While any type of fasteners may be used to keep the conductive socks 12, 14 in place, in an embodiment of the invention shown in FIG. 1, an elastic band 15 is used to secure the inner sock 12 and hook and loop fasteners 17 are used to secure the outer sock 14.

In one embodiment of the invention, a first conductive tab 16 is attached to a lower end of the outer sock 14. During the testing process, the first conductive tab 16 will receive a ground lead providing a path through the conductive outer sock 14 to ground. A second conductive tab 20 is attached to an upper end of the inner sock 12 on a side of the insulating liner 10 which is opposite the first conductive tab 16.

The second conductive tab 20 will receive a high voltage lead during the testing process that will provide an electrical potential to the conductive inner sock 12. The insulating liner 10, preferably with the inner sock 12 and the outer sock 14 installed, are placed on an arc suppression blanket 18. During the testing of the dielectric properties of the insulating liner 10, if any failures are present in the insulating liner 10, the electrical potential will flow from the inner sock 12 through the insulating liner 10 walls to the outer sock 14 then through the ground lead connected at the first conductive tab 16. The arc suppression blanket 18 serves to prevent arcing or ground leakage in the case of a positive test where electrical current passes through the walls of the insulating liner 10 and electrifies the outer sock 14. The arc suppression blanket 18 preferably extends from all bottom edges of the insulating liner 10 by at least six inches. Preventing electrical current from reaching the ground during the testing process is necessary for the protection of the individuals performing the test.

Figure 2:
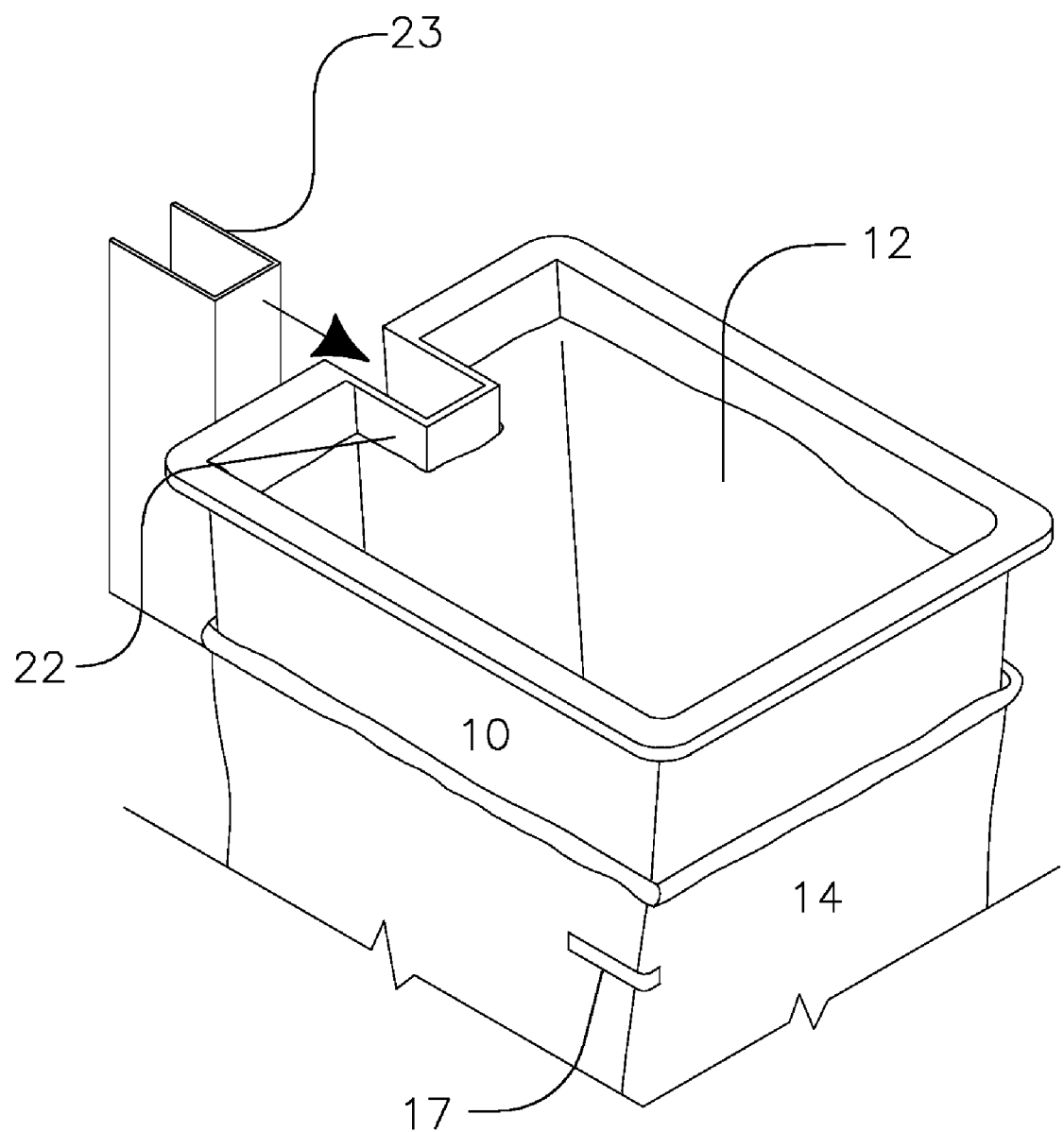
FIG. 2 is a partial perspective view of an insulating liner with conductive socks disposed along its inner and outer surfaces in accordance with an embodiment of the invention.
Figure 3:
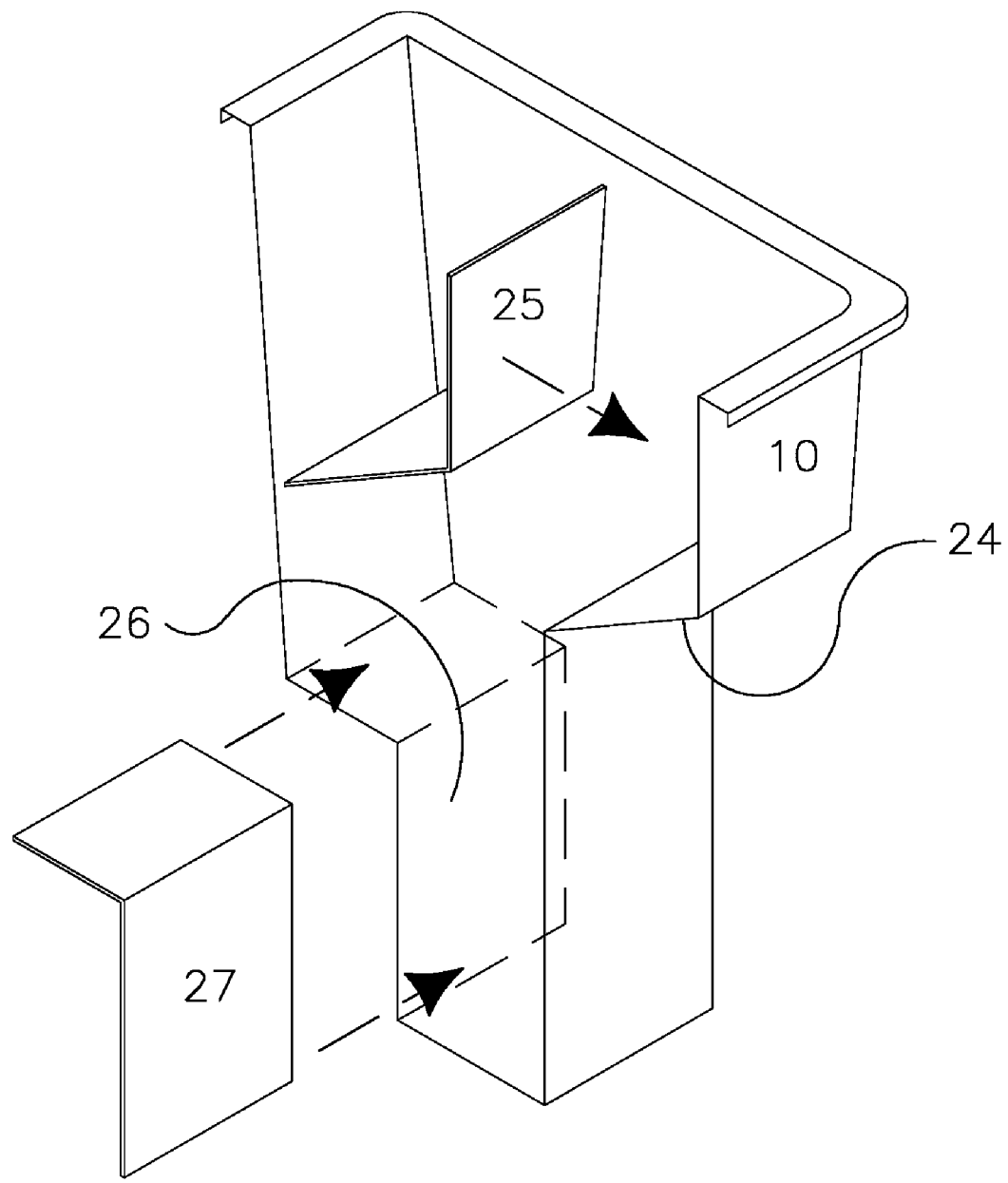
FIG. 3 is a partial sectional view of an insulating liner with conductive socks disposed along its inner and outer surfaces in accordance with an embodiment of the invention.

Referring to now to FIGS. 2 and 3, insulating liners come in many different shapes and sizes. In FIGS. 2 and 3, purely by way of example, two insulating liners each having different shapes are shown. Different insulating liners 10 are designed to fit specific buckets installed on lift equipment from different manufacturers. Design considerations for the lift equipment and the convenience of the operator in the bucket dictate various design features that may affect the shape of the insulating liner's 10 inner or outer surfaces.

In FIG. 2, there is shown insulating liner having a recess 22 for attaching a boom. The recess 22 extends into the interior volume of the insulating liner 10. In such an embodiment, the conductive socks 12, 14 are disposed along inner and outer surfaces of the insulating liner 10.

In FIG. 3, the insulating liner 10 includes a tool shelf 24 and a molded step 26. Contours in a surface of the insulating liner 10 can prevent continuity between the inner sock 12 or the outer sock 14 and the surface of the insulating liner 10. Therefore, in accordance with an embodiment of the invention, conductive mats with conductive adhesive are installed over irregularities in the surface of the insulating liner 10 before installing the inner sock 12 or the outer sock 14. The conductive mats with conductive adhesive are preferably adhered to an inner or outer surface of the liner 10 as needed to maintain continuity at all surfaces of the insulating liner 10.

Conductive mats may be made to fit over recesses designed to accept the boom 23 as in FIG. 2 and/or to fit into a tool shelf 25 or a molded step 26 as in FIG. 3. Ensuring continuity between the inner sock 12 or the outer sock 14 and the insulating liner's 10 surface maintains the integrity of the electrical testing and provides results comparable to traditional methods of testing in liquid.

Figure 4:
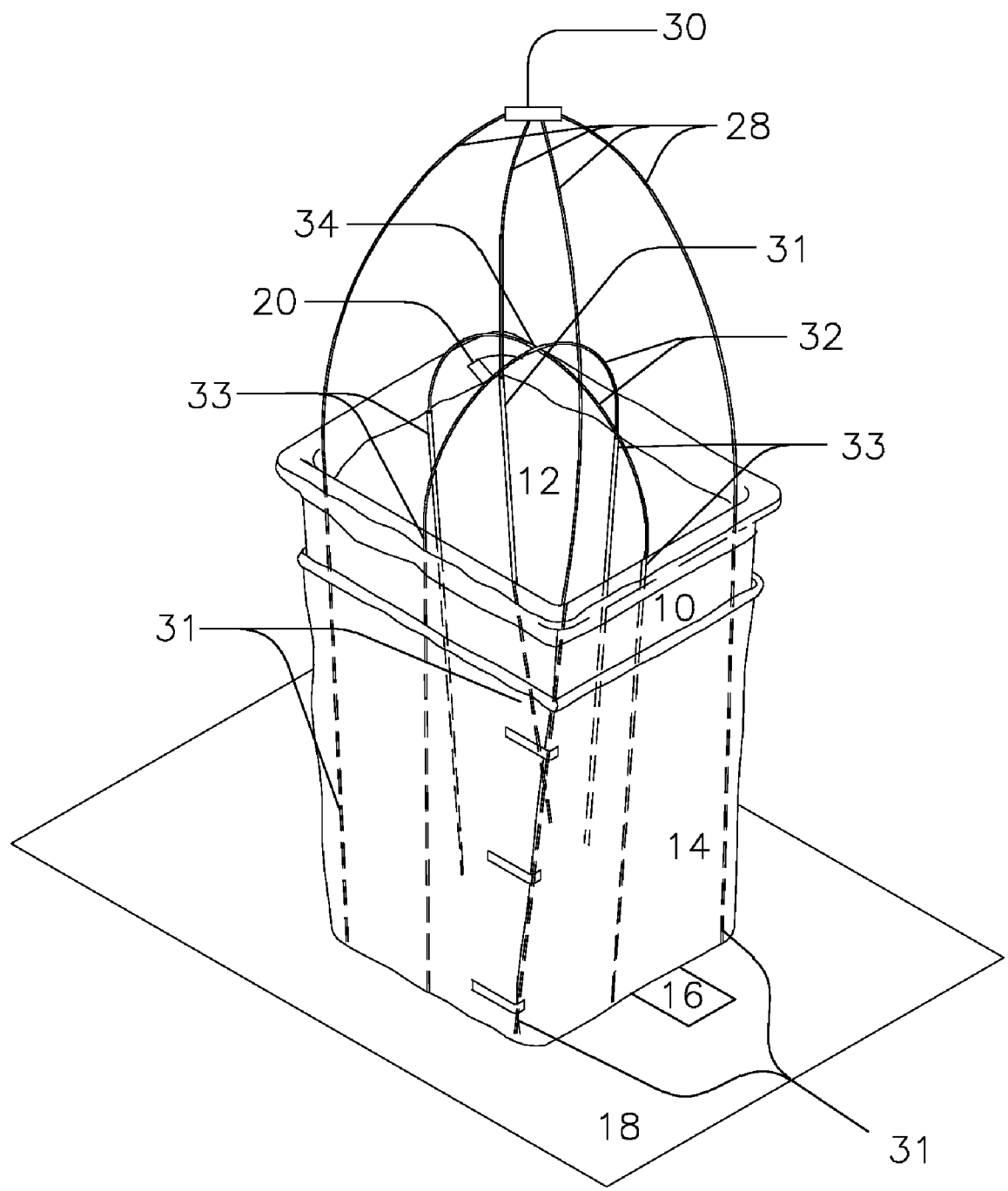
FIG. 4 is an isometric view of an insulating liner having components of an embodiment of the invention disposed therewith such that the insulating liner is ready for testing.

Referring now to FIG. 4, an embodiment of the invention ready for testing is shown. The insulating liner 10 is fitted with its inner sock 12 and its outer sock 14. Conductive tab 16 is attached to the outer sock 14. Conductive tab 20 is attached to the inner sock 12. The inner sock 12 is fitted with a plurality of sleeves 31 designed to receive a first set of flexible rods 28. In this example, the first set of flexible rods 28 are inserted into a matching number of sleeves 31 which are disposed along the longitudinal edges of the inner sock 12 at the edges where the walls of the insulating liner 10 meet. The upper ends of the first set of flexible rods 28 are then bent so that the upper ends converge over the top edge of the insulating liner 10 and are connected by a first coupling 30. In one embodiment, this coupling could be equipped with dielectric arms capable of holding excess cable from the high voltage lead. In this example, sock 12 is fitted with a plurality of sleeves 33 designed to receive a second set of flexible rods 32. The second set of flexible rods 32 are inserted into a matching number of sleeves 33 that are disposed along the longitudinal side of the inner sock 12 at a point near the midpoint of a face defined by the sides of the insulating liner 10. The upper ends of the second set of flexible rods 32 are then bent in such a way that the upper ends converge over the top edge of the insulating liner 10 and are connected by a second coupling 34. The tension of the rods ensures that continuity is maintained between the inner sock 12 and the inner surface of the insulating liner 10.

Figure 5:
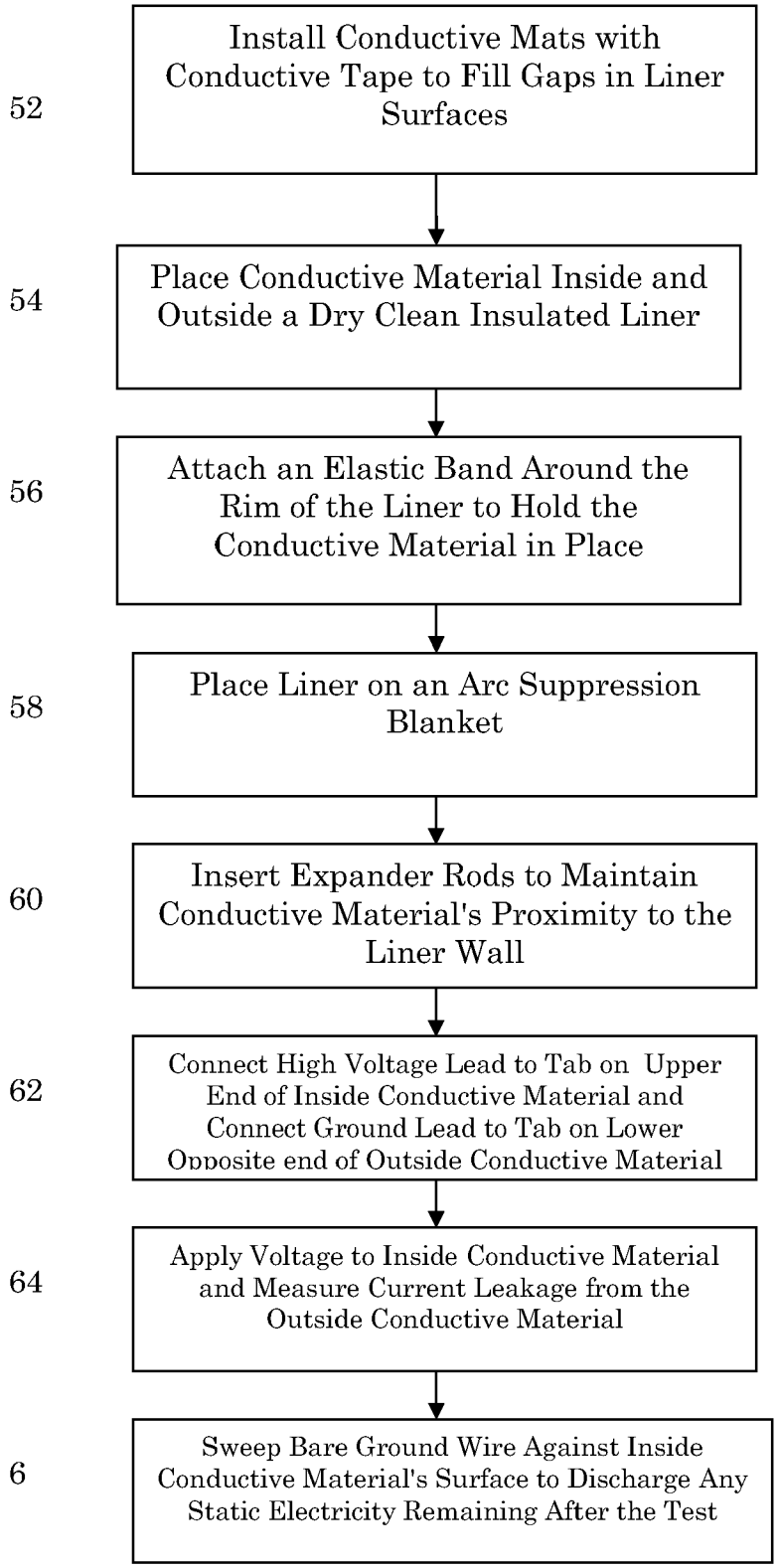
FIG. 5 is a flow diagram of a method for dry testing an insulating liner in accordance with an embodiment of the invention.

Referring now to FIG. 5, a flow diagram of a method 50 for dry testing an insulating liner in accordance with an embodiment of the invention is shown.

The method 50 begins with filling any gaps caused by contour features on the insulating liner's surface with conductive mats that are connected to the liner with a conductive adhesive (step 52). Step 52 is preferable in order to maintain the integrity of the electrical test by insuring that all liner surfaces are tested. After filling any gaps in the inner and outer surfaces of the liner conductive socks are placed along inner and outer surfaces of an insulating liner (step 54). The outer sock can be installed by inverting the insulating liner and sliding the outer sock over the external surface of the insulating liner. The inner liner can be installed by inserting it into the interior of the insulating liner. The liner should be dry and clean to prevent foreign material from affecting the dielectric properties of the insulating liner and to prolong the life of the conductive material.

Once the socks are in place, a non-conductive elastic band (or any type of fastener) is preferably installed around the upper edge of the insulating liner (step 56). The elastic band will help hold the top edges of the socks in place while keeping the two conductive surfaces isolated from each other. As described above, any type of fastener may be used and the location of the fastener may vary as a function of the type of fastener being used.

The liner, with socks installed, is then placed on an arc suppressing blanket that prevents electric current from arcing from the outer sock to ground or leakage of current from the outer sock directly to ground (step 58).

Next, in step 60, expander rods are preferably inserted into the inner and outer socks to expand and maintain their shape to correspond to the inner and outer surfaces of the insulating liner. Once step the above-described steps are complete, the insulating liner is ready for dry testing.

After the insulating liner is prepared for testing, a high voltage lead is attached to the tab located at the top end of the inner sock, while a ground lead is attached to the tab located at the bottom edge of the outer sock (step 62). A high AC or DC voltage is then applied to a conductive tab connected to the inside sock (step 64).

A current measuring device, preferably connected to the outer sock and ground, indicates whether voltage passed through the material of the insulating liner. After the test has been performed, a bare ground cable from the high voltage source box is swept across the surfaces of the inside sock, preferably at a rate of three minutes per 10,000 Volts. This discharges any static electricity built up in the conductive inner sock (step 66).

Although the features and elements of the present invention are described in the preferred embodiments in particular combinations, each feature or element can be used alone without the other features and elements of the preferred embodiments or in various combinations with or without other features and elements of the present invention.

What is claimed is:

1. An apparatus for dry testing dielectric properties of a material comprising:
    a first conductive material disposed along a first surface of a material being tested;
    a second conductive material disposed along a second surface of said material being tested;
    a first conductive tab attached to said first conductive material for attaching a test lead;
    a second conductive tab attached to said second conductive material for attaching a test lead where said second tab is located on the opposite end of said material being tested relative to said first conductive tab;
    an arc suppression blanket placed between said material being tested and a testing surface;
    a plurality of sleeves attached to longitudinal edges of said first conductive material for receiving a plurality of flexible expansion rods; and
    said plurality of flexible expansion rods attached at their upper ends by a coupling.

2. The apparatus of claim 1 further comprising:
    a conductive mat inserted between either said first or second conductive material and surface variations in said material being tested;
    a conductive adhesive attaching said conductive mat to said material being tested.

3. The apparatus of claim 1 wherein said first and second conductive material is a woven polyester fabric plated with an electrical conductor.

4. The apparatus of claim 1 wherein the material being tested is a lift bucket liner.

5. A method of dry testing dielectric properties of a material comprising the steps of:
    applying a first conductive material disposed along a first surface of a material being tested;
    applying a second conductive material disposed along a second surface of said material being tested;
    connecting a first conductive tab to said first conductive material for attaching a test lead;
    connecting a second conductive tab to said second conductive material for attaching a test lead where said second tab is located on the opposite end of said material being tested relative to said first conductive tab;
    placing an arc suppression blanket between said material being tested and a testing surface;
    applying a high voltage to said first conductive tab;
    connecting said second conductive tab to an electrical ground;
    measuring electric current between said second conductive material and said electrical ground;
    attaching a plurality of sleeves to longitudinal edges of said first conductive material for receiving a plurality of flexible expansion rods; and
    attaching a plurality of flexible expansion rods at their upper ends by a coupling.

6. The method of claim 5 further comprising the steps of:
    inserting a conductive mat between either said first or second conductive material and surface variations in said material being tested;
    attaching with conductive adhesive said conductive mat to said material being tested.

* * * * *